(12) United States Patent
Shen et al.

(10) Patent No.: US 11,584,857 B2
(45) Date of Patent: Feb. 21, 2023

(54) PHOSPHATE SURFACTANT COMPOSITIONS

(71) Applicant: Dow Global Technologies LLC, Midland, MI (US)

(72) Inventors: Cheng Shen, Shanghai (CN); Jieying Chen, Shanghai (CN); Zeyu Zhong, Shanghai (CN)

(73) Assignee: Dow Global Technologies LLC, Midland, MI (US)

(*) Notice: Subject to any disclaimer, the term of this patent is extended or adjusted under 35 U.S.C. 154(b) by 220 days.

(21) Appl. No.: 17/251,854

(22) PCT Filed: Jun. 27, 2018

(86) PCT No.: PCT/CN2018/093086
§ 371 (c)(1),
(2) Date: Dec. 14, 2020

(87) PCT Pub. No.: WO2020/000252
PCT Pub. Date: Jan. 2, 2020

(65) Prior Publication Data
US 2021/0253869 A1    Aug. 19, 2021

(51) Int. Cl.
*C09D 5/02* (2006.01)
*C09D 7/63* (2018.01)
*C07F 9/09* (2006.01)
*C08K 5/521* (2006.01)

(52) U.S. Cl.
CPC .............. *C09D 5/027* (2013.01); *C07F 9/091* (2013.01); *C09D 5/022* (2013.01); *C09D 7/63* (2018.01); *C08K 5/521* (2013.01)

(58) Field of Classification Search
CPC .......... C09D 5/027; C09D 5/022; C09D 7/63; C08K 5/521; C07F 9/091
USPC ......................................................... 524/145
See application file for complete search history.

(56) References Cited

U.S. PATENT DOCUMENTS

| | | | |
|---|---|---|---|
| 3,963,635 A | 6/1976 | Dawson et al. | |
| 6,346,509 B1 | 2/2002 | Kadono et al. | |
| 6,900,265 B2 | 5/2005 | Schultz et al. | |
| 7,074,972 B2 | 7/2006 | Maas et al. | |
| 7,183,446 B2 | 2/2007 | Zeller et al. | |
| 8,273,414 B2 | 9/2012 | Daniels et al. | |
| 8,519,071 B2 | 8/2013 | Schliwka et al. | |
| 8,822,580 B2 | 9/2014 | Korenkiewicz et al. | |
| 10,800,927 B2 * | 10/2020 | Qian .................... | C09D 125/14 |
| 2003/0176745 A1 | 9/2003 | Maas et al. | |
| 2004/0030200 A1 | 2/2004 | Zeller et al. | |
| 2008/0051289 A1 * | 2/2008 | Alexander ............ | C11D 3/362 |
| | | | 504/358 |
| 2011/0212870 A1 | 9/2011 | Lant | |
| 2011/0259583 A1 | 10/2011 | Bittner et al. | |
| 2012/0316273 A1 | 12/2012 | Korenkiewicz et al. | |

FOREIGN PATENT DOCUMENTS

| | | | |
|---|---|---|---|
| CN | 1950408 | | 4/2007 |
| CN | 1950408 A | | 4/2007 |
| CN | 106632739 A | * | 5/2017 |
| JP | 2003040915 A | | 2/2003 |
| JP | 2007270414 A | | 10/2007 |
| JP | 2017048315 | * | 3/2017 |
| JP | 2017048315 A | | 3/2017 |

OTHER PUBLICATIONS

Translation of CN 106632739, May 10, 2017. (Year: 2017).*
International Search Report & Written Opinion for related PCT Application PCT/CN2018/093086, dated Mar. 19, 2019 (11 pgs).

* cited by examiner

*Primary Examiner* — Hui H Chin
(74) *Attorney, Agent, or Firm* — Brooks, Cameron & Huebsch, PLLC

(57) ABSTRACT

A phosphate surfactant composition including a phosphate surfactant formed from a secondary alcohol alkoxylate.

4 Claims, 1 Drawing Sheet

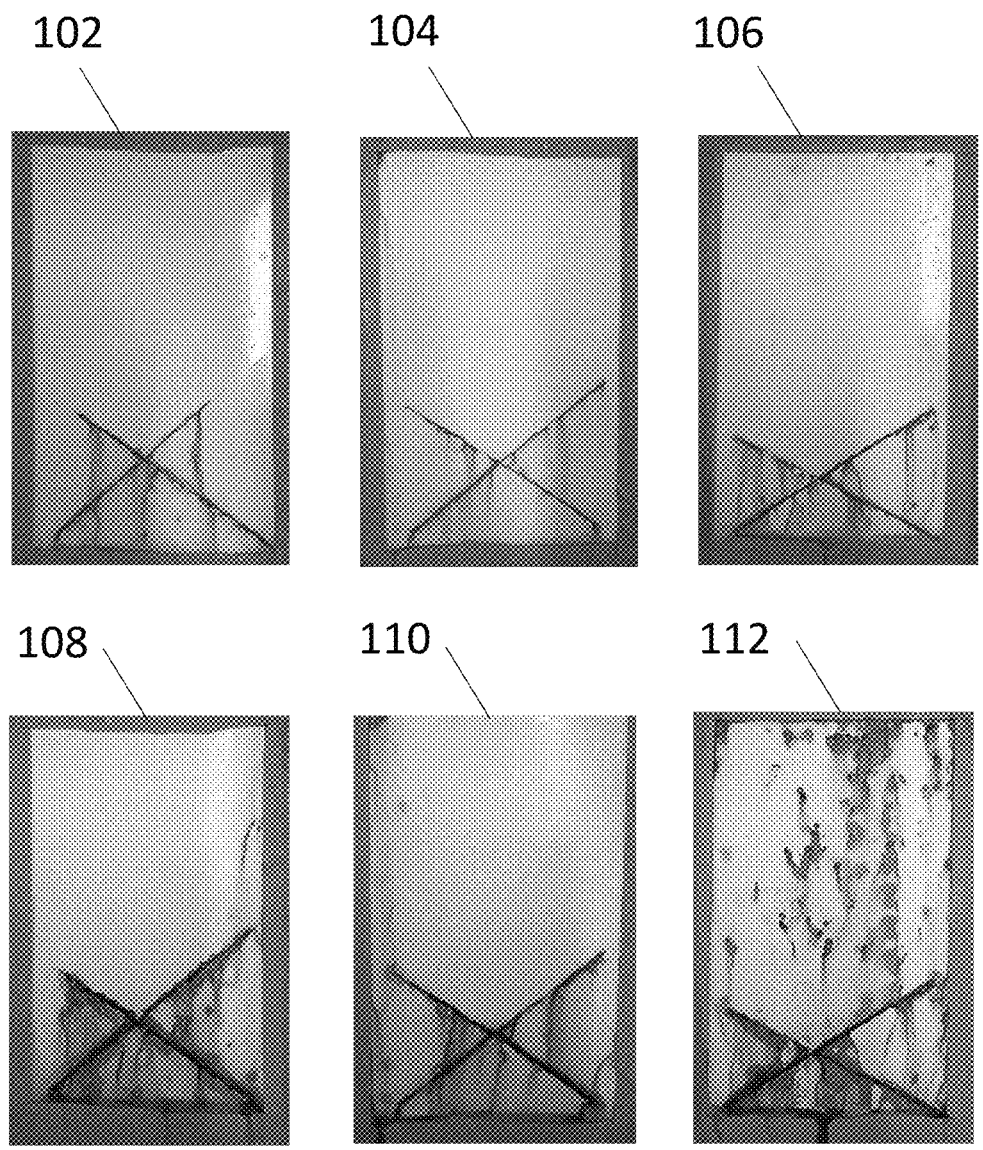

PHOSPHATE SURFACTANT COMPOSITIONS

This application is a National Stage Application under 35 U.S.C. § 371 of International Application Number PCT/CN2018/093086, filed Jun. 27, 2018 and published as WO 2020/000252 on Jan. 2, 2020, the entire contents of which are incorporated herein by reference in its entirety

FIELD OF DISCLOSURE

Embodiments of the present disclosure are directed towards phosphate surfactant compositions, more specifically, embodiments are directed towards phosphate surfactant compositions including a phosphate surfactant formed from a secondary alcohol alkoxylate.

BACKGROUND

Surfactants may be utilized for a number of applications including emulsion polymerizations, coatings, agricultural formulations, fragrance emulsions, degreasing, and metal processing, among others. There is continued focus in the industry on developing new and improved surfactants.

SUMMARY

The present disclosure provides phosphate surfactant compositions that include a phosphate surfactant represented by Formula I:

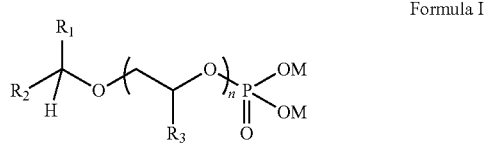

Formula I wherein $R_1$ and $R_2$ are each independently hydrogen or a linear or branched alkyl group having from 1 to 18 carbon atoms, such that a combination of $R_1$ and $R_2$ includes from 8 to 18 carbon atoms; $R_3$ is hydrogen or an alkyl radical containing from 1 to 6 carbon atoms; n is an integer from 1 to 50; and each M is independently hydrogen, an alkali metal atom, an alkaline earth metal atom, an ammonium group, or a substituted ammonium group;
a phosphate surfactant represented by Formula II:

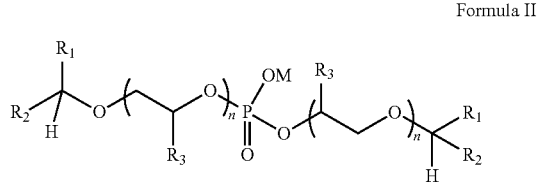

Formula II wherein each $R_1$ and $R_2$ is independently hydrogen or a linear or branched alkyl group having from 1 to 18 carbon atoms, such that combinations of $R_1$ and $R_2$ bonded to a same carbon atom include from 8 to 18 carbon atoms; each $R_3$ is independently hydrogen or an alkyl radical containing from 1 to 6 carbon atoms; n is an integer from 1 to 50; and M is hydrogen, an alkali metal atom, an alkaline earth metal atom, an ammonium group, or a substituted ammonium group; or combinations thereof.

The present disclosure provides emulsions formed with the phosphate surfactant compositions.

The present disclosure provides coatings formed with the emulsions disclosed herein.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 1 shows salt spray resistance images.

DETAILED DESCRIPTION

Phosphate surfactant compositions are disclosed herein. Embodiments of the present disclosure provide that the phosphate surfactant compositions are substantially free of alkyl phenol ethoxylates.

Alkyl phenol ethoxylates have previously been utilized as surfactants. However, there is a growing market need for surfactant compositions are substantially free of alkyl phenol ethoxylates due to a number of issues associated with alkyl phenol ethoxylates including various governmental regulations, among others.

As mentioned, the phosphate surfactant compositions disclosed herein are substantially free of alkyl phenol ethoxylates. As used herein, "substantially free of alkyl phenol ethoxylates" refers to less than 5 percent by weight of alkyl phenol ethoxylate based upon a total weight of the phosphate surfactant composition. For instance, the phosphate surfactant compositions may include 0 percent by weight, based upon a total weight of the phosphate surfactant composition, of alkyl phenol ethoxylates. In other words, the phosphate surfactant compositions may include no alkyl phenol ethoxylates.

The phosphate surfactant compositions disclosed herein can have one or more properties that are desirable for various applications. For instance, the phosphate surfactant compositions disclosed herein may have an improved, i.e. reduced, critical micelle concentration as compared to other phosphate surfactants. The phosphate surfactant compositions disclosed herein can be utilized for a number of different applications.

Critical micelle concentration (CMC) is a concentration of a surfactant above which micelles start to form. The CMC can be an important characteristic for surfactants for a number of applications. For instance, as surface tension does not reduce further above the CMC, in many processes the CMC can be utilized to specify the limiting concentration of surfactant. Additionally, for some applications e.g., cleaning applications, the CMC can be utilized as an indicator of efficiency of a surfactant.

The phosphate surfactant compositions disclosed herein may have an improved, i.e. reduced, foam height as compared to other phosphate surfactants. For a number of applications, e.g., latex paint, automatic dishwashing, among others, decreased foam is desirable.

The phosphate surfactant compositions disclosed herein can include a phosphate surfactant represented by Formula I:

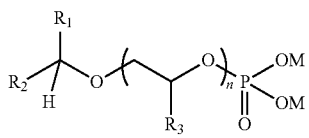

Formula I wherein $R_1$ and $R_2$ are each independently hydrogen or a linear or branched alkyl group having from 1 to 18 carbon atoms, such that a combination of $R_1$ and $R_2$ includes from 8 to 18 carbon atoms; $R_3$ is hydrogen or an alkyl radical containing from 1 to 6 carbon atoms; n is an integer from 1 to 50; and each M is independently hydrogen, an alkali metal atom, an alkaline earth metal atom, an ammonium group, or a substituted ammonium group.

All individual values and subranges from 8 to 18 carbon atoms are included; for example, the combination of $R_1$ and $R_2$ can include from a lower limit of 8, 10, or 12 carbon atoms to an upper limit of 18, 16, or 14 carbon atoms. For instance, the combination of $R_1$ and $R_2$ can include from 8 to 16, 8 to 14, 10 to 18, 10 to 16, 10 to 14, 12 to 18, 12 to 16, or 12 to 14 carbon atoms.

All individual values and subranges from 1 to 50 are included; for example, n can an integer from a lower limit of 1, 2, 3, or 4 to an upper limit of 50, 35, 25, or 15.

The phosphate surfactant compositions disclosed herein can include a phosphate surfactant represented by Formula II:

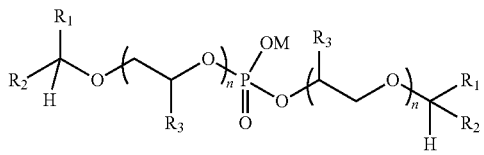

Formula II wherein each $R_1$ and $R_2$ is independently hydrogen or a linear or branched alkyl group having from 1 to 18 carbon atoms, such that combinations of $R_1$ and $R_2$ bonded to a same carbon atom include from 8 to 18 carbon atoms; each $R_3$ is independently hydrogen or an alkyl radical containing from 1 to 6 carbon atoms; n is an integer from 1 to 50; and M is hydrogen, an alkali metal atom, an alkaline earth metal atom, an ammonium group, or a substituted ammonium group.

All individual values and subranges from 8 to 18 carbon atoms are included; for example, the combination of $R_1$ and $R_2$ can include from a lower limit of 8, 10, or 12 carbon atoms to an upper limit of 18, 16, or 14 carbon atoms. For instance, the combination of $R_1$ and $R_2$ can include from 8 to 16, 8 to 14, 10 to 18, 10 to 16, 10 to 14, 12 to 18, 12 to 16, or 12 to 14 carbon atoms.

All individual values and subranges from 1 to 50 are included; for example, n can an integer from a lower limit of 1, 2, 3, or 4 to an upper limit of 50, 35, 25, or 15.

The phosphate surfactants disclosed herein, i.e. the phosphate surfactants represented by Formula I and Formula II, can be formed from a secondary alcohol alkoxylate, e.g. a secondary alcohol ethoxylate. The secondary alcohol alkoxylate represented by Formula III:

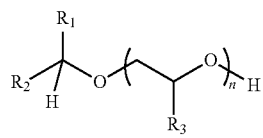

Formula III wherein $R_1$ and $R_2$ are each independently hydrogen or a linear or branched alkyl group having from 1 to 18 carbon atoms, such that a combination of $R_1$ and $R_2$ includes from 8 to 18 carbon atoms; $R_3$ is hydrogen or an alkyl radical containing from 1 to 6 carbon atoms; and n is an integer from 1 to 50.

All individual values and subranges from 8 to 18 carbon atoms are included; for example, the combination of $R_1$ and $R_2$ can include from a lower limit of 8, 10, or 12 carbon atoms to an upper limit of 18, 16, or 14 carbon atoms. For instance, the combination of $R_1$ and $R_2$ can include from 8 to 16, 8 to 14, 10 to 18, 10 to 16, 10 to 14, 12 to 18, 12 to 16, or 12 to 14 carbon atoms.

All individual values and subranges from 1 to 50 are included; for example, n can an integer from a lower limit of 1, 2, 3, or 4 to an upper limit of 50, 35, 25, or 15.

The secondary alcohol alkoxylate represented by Formula III can be prepared using known equipment, reaction components, and reaction conditions. The secondary alcohol alkoxylate represented by Formula III may be obtained commercially. Examples of commercially available secondary alcohol alkoxylates represented by Formula III include, but are not limited to, ECOSURF™ LF-30 and ECOSURF™ LF-45, both available from The Dow Chemical Company, as well as TERGITOL™ 15-S-5 and TERGITOL™ 15-S-7, which are secondary alcohol ethoxylates, both available from The Dow Chemical Company.

The phosphate surfactants represented by Formula I and Formula II can be formed by a phosphorylation process. For example, in forming the phosphate surfactants represented by Formula I and Formula II, the secondary alcohol alkoxylate represented by Formula III can be reacted with polyphosphoric acid ($H_3PO_4$) and phosphorous pentoxide ($P_2O_5$). The phosphorylation process can be performed using known equipment, additional reaction components, and reaction conditions.

The secondary alcohol alkoxylate represented by Formula III can be reacted with polyphosphoric acid at a mole ratio from 5:1 to 1:5 moles of the secondary alcohol alkoxylate to moles of polyphosphoric acid. The secondary alcohol alkoxylate represented by Formula III can be reacted with phosphorous pentoxide at a mole ratio from 5:1 to 1:5 moles of the secondary alcohol alkoxylate to moles of phosphorous pentoxide. The secondary alcohol alkoxylate represented by Formula III can be reacted with the polyphosphoric acid and the phosphorous pentoxide sequentially, i.e., the secondary alcohol alkoxylate can be reacted with polyphosphoric acid and then subsequently the polyphosphoric pentoxide can be added; or the secondary alcohol alkoxylate can be reacted with phosphorous pentoxide and then subsequently the polyphosphoric acid can be added. The secondary alcohol alkoxylate represented by Formula III can be reacted with the polyphosphoric acid and the phosphorous pentoxide simultaneously; i.e. the secondary alcohol alkoxylate, the phosphoric acid, and the phosphorous pentoxide can be combined for the phosphorylation process.

As the secondary alcohol alkoxylate represented by Formula III is utilized to form the phosphate surfactants represented by Formula I and Formula II, the phosphate surfactant compositions disclosed herein may include the secondary alcohol alkoxylate represented by Formula III, e.g., unreacted reactant.

The phosphate surfactant compositions disclosed herein can include from 20 to 99.9 weight percent of the phosphate surfactant represented by Formula I based upon a total weight of the phosphate surfactant composition. All individual values and subranges from 20 to 99.9 weight percent are included; for example, the phosphate surfactant composition can include from a lower limit of 20, 21, 22, 23, 24, 25, 27, 28, or 30 weight percent to an upper limit of 99.9, 95, 90, 85, 80, 75, 70, 65, or 60 weight percent of the phosphate surfactant represented by Formula I based upon a total weight of the phosphate surfactant composition.

The phosphate surfactant compositions disclosed herein can include from 0.1 to 80 weight percent of the phosphate surfactant represented by Formula II based upon a total weight of the phosphate surfactant composition. All individual values and subranges from 0.1 to 80 weight percent are included; for example, the phosphate surfactant composition can include from a lower limit of 0.1, 0.3, 0.5, or 1.0 weight percent to an upper limit of 80, 60, 40, or 20 weight percent of the phosphate surfactant represented by Formula II based upon a total weight of the phosphate surfactant composition.

The phosphate surfactant compositions disclosed herein can include from 0.01 to 10 weight percent of the secondary alcohol alkoxylate represented by Formula III based upon a total weight of the phosphate surfactant composition. All individual values and subranges from 0.01 to 10 weight percent are included; for example, the phosphate surfactant composition can include from a lower limit of 0.01, 0.1, or 0.5 weight percent to an upper limit of 10, 7.5, or 5 weight percent of the secondary alcohol alkoxylate represented by Formula III based upon a total weight of the phosphate surfactant composition.

The phosphate surfactant compositions disclosed herein can be aqueous or non-aqueous. As used herein, a non-aqueous phosphate surfactant composition refers to a composition having a water concentration that is less than 0.1 weight percent based upon a total weight of the phosphate surfactant composition. When water is included, the phosphate surfactant compositions disclosed herein can include from 0.1 to 80 weight percent of water based upon a total weight of the phosphate surfactant composition. All individual values and subranges from 0.1 to 80 weight percent are included; for example, the phosphate surfactant composition can include from a lower limit of 0.1, 1, 3, 5, 10, 15, 20, 35, or 40 weight percent to an upper limit of 80, 77, 75, 72, 70, 65, or 60 weight percent of water based upon a total weight of the phosphate surfactant composition.

The phosphate surfactant compositions disclosed herein can be utilized with one or more known surfactants. Different amounts of one or more known surfactants may be utilized for various applications. For example, an alkyl alkoxylate surfactant with the formula: $R^4O(AO)_zH$, where, $R^4$ is a $C_6$ to $C_{24}$ linear or branched alkyl, and AO is a $C_2$ to $C_4$ alkylene oxide; and z is from 1-50. The alkyl alkoxylate surfactant with the formula: $R^4O(AO)_zH$ can be utilized with the phosphate surfactant compositions from 0.01 to 70 weight percent based upon a total weight of the phosphate surfactant composition. All individual values and subranges from 0.01 to 70 weight percent are included; for example, the alkyl alkoxylate surfactant with the formula: $R^4O(AO)_zH$ can be utilized from a lower limit of 0.01, 3.0, or 5.0 weight percent to an upper limit of 70, 50, or 30 weight percent based upon a total weight of the phosphate surfactant composition.

The phosphate surfactant compositions disclosed herein can have a solids content from 20 to 100 weight percent based upon a total weight of the phosphate surfactant composition. All individual values and subranges from 20 to 100 weight percent are included; for example, the phosphate surfactant composition can have a solids content from a lower limit of 20, 25, or 30 weight percent to an upper limit of 100, 95, or 90 weight percent based upon a total weight of the phosphate surfactant composition.

As mentioned, the phosphate surfactant compositions disclosed herein may have an improved, i.e. reduced, critical micelle concentration as compared to other phosphate surfactants. A reduced critical micelle concentration is desirable for a number of applications. The phosphate surfactant compositions can have a critical micelle concentration from 50 to 1000 ppm. All individual values and subranges from 50 to 1000 ppm are included; for example, the phosphate surfactant composition can have a critical micelle concentration from a lower limit of 50, 60, 75, 85, 100, 110, 120, 130, 140, 145, 150, or 160 ppm to an upper limit of 1000, 900, 800, 700, 600, 500, 400, 300, 245, 235, 225, or 215 ppm.

Further, as mentioned, the phosphate surfactant compositions disclosed herein may have an improved, i.e. reduced, foam height as compared to other phosphate surfactants. A reduced foam height is desirable for a number of applications. The phosphate surfactant compositions can have a foam height, as determined by Ross-Miles Foam Height test according to GB/T-7462-94 at 0.2 wt % and reported at 0 minutes, from 110 to 140 mm. All individual values and subranges from 110 to 140 mm are included; for example, the phosphate surfactant composition can have a foam height, as determined by Ross-Miles Foam Height test according to GB/T-7462-94 at 0.2 wt % and reported at 0 minutes, from a lower limit of 110, 115, or 120 mm to an upper limit of 140, 138, or 136 mm. The phosphate surfactant compositions can have a foam height, as determined by Ross-Miles Foam Height test according to GB/T-7462-94 at 0.2 wt % and reported at 5 minutes, from 20 to 130 mm. All individual values and subranges from 20 to 130 mm are included; for example, the phosphate surfactant composition can have a foam height, as determined by Ross-Miles Foam Height test according to GB/T-7462-94 at 0.2 wt % and reported at 5 minutes, from a lower limit of 20, 30, 40, 50, 60, 70, 80, 90, or 95 mm to an upper limit of 130, 128, 127, 125, 123, 122, 121, or 120 mm.

The phosphate surfactant compositions disclosed herein can be utilized to form emulsions, which may be referred to as dispersions, e.g., monomers emulsified in a continuous phase of water. The emulsions can be prepared with monomers by conventional emulsion polymerization including known emulsion polymerization components and reaction conditions, for instance. Examples of monomers include, but are not limited to, styrene, ethylhexyl acrylate, methacrylic acid, methyl methacrylate, butyl acrylate, acrylamide, acrylic acid, ethylene, propylene, 1-butene, 3-methyl-1-butene, 4-methyl-1-pentene, 3-methyl-1-pentene, 1-heptene, 1-hexene, 1-octene, 1-decene, 1-dodecene, hexyl acrylate, octyl acrylate, isooctyl acrylate, n-decyl acrylate, isodecyl acrylate, tert-butyl acrylate, hexyl methacrylate, isobutyl methacrylate, isopropyl methacrylate, 2-hydroxyethyl acrylate, and combinations thereof, among others. The monomers may be reacted to form homopolymers and/or copolymers. The emulsion polymerization can be performed using free-radical producing initiators, which may be utilized in an amount from 0.01 percent to 5 percent based on a total weight of the monomers, for instance.

Optionally, other ingredients known for emulsion polymerizations may be utilized, such as chelating agents, buffering agents, inorganic salts, and pH adjusting agents, among others. Various amounts other ingredients may be utilized for different applications.

The emulsions disclosed herein, i.e., formed with the phosphate surfactant compositions disclosed herein, can have a solids content from 25 to 65 weight percent based upon a total weight of the emulsion. All individual values and subranges from 25 to 65 weight percent are included; for example, the emulsion can have a solids content from a lower limit of 25, 30, 35, 37, or 40 weight percent to an upper limit of 65, 63, 60, 58, or 55 weight percent based upon a total weight of the emulsion.

One or more embodiments of the present disclosure provide that the emulsion has an average particle size from 10 nm to 500 nm. All individual values and subranges from 10 nm to 500 nm are included; for example, the emulsion can have a an average particle size from a lower limit of 10, 25, or 50 nm to an upper limit of 500, 300, or 150 nm.

The emulsions formed from the phosphate surfactant compositions disclosed herein can be utilized to form coatings. These coatings may be used for a number of different coating applications such as industrial coating applications, architectural coating applications, automotive coating applications, outdoor furniture coating applications, among others.

Advantageously, the coatings disclosed herein can have one or more properties that are desirable for various applications. For instance, the coatings disclosed herein may have an improved color development, e.g., a reduced color difference between touched portions of the coatings and untouched portions of the coatings, as compared to other coatings.

Also, the coatings disclosed herein may have an improved gloss, e.g., greater, or comparable gloss, as compared to other coatings.

The coatings disclosed herein, i.e., formed with the emulsions disclosed herein, can be prepared by conventional coating forming processes including known coating components and conditions, for instance. For example, the coatings can be prepared by combining the emulsion with one or more coating components. Examples of coating components include, but are not limited to, thickeners, fillers, pH adjusters, dispersants, wetting agents, defoamers, colorants, biocides, flowing agents, crosslinkers, anti-oxidants, plasticizers, leveling agents, thixotropic agents, adhesion promoters, and preservatives. Different amounts of one or more coating components may be utilized for various applications.

The coatings may be applied to one or more surfaces of an article or a structure via any method. Such methods include, but are not limited to, spraying, dipping, rolling, and any other conventional technique generally known to those skilled in the art. The surface of such structures to be coated with the coating composition may comprise concrete, wood, metal, plastic, glass, drywall, among others. Known equipment, components, and conditions may be utilized when applying the coatings. The coatings can form one or more layers having various thicknesses for different applications.

EXAMPLES

In the Examples, various terms and designations for materials are used including, for instance, the following:

TERGITOL™ 15-S-5 (secondary alcohol alkyl alkoxylate of Formula III, wherein a combination of $R_1$ and $R_2$ includes from 12 to 14 carbon atoms; n is 5; and $R_3$ is hydrogen, obtained from The Dow Chemical Company); TERGITOL™ 15-S-7 (secondary alcohol alkyl alkoxylate of Formula III, wherein a combination of $R_1$ and $R_2$ includes from 12 to 14 carbon atoms; n is 7; and $R_3$ is hydrogen, obtained from The Dow Chemical Company); polyphosphoric acid (obtained from SinoPharma Co. Ltd.); phosphorous pentoxide (obtained from SinoPharma Co. Ltd.); RHODAFAC® RS-610S25 (phosphate surfactant, sodium phosphate of isotridecyl ethoxylate, obtained from Solvay).

Example 1, a phosphate surfactant composition, was formed as follows. TERGITOL™ 15-S-5 (104.8 grams, 0.25 mol) was added to a container, under nitrogen, that was maintained at 35° C. and constantly stirred. Polyphosphoric acid (15.0 g, 0.175 mol) was incrementally added to the contents of the container over 30 minutes, the temperature was increased to 45° C., the contents of the container were constantly stirred. Phosphorous pentoxide (5.3 g, 0.075 mol) was added to the contents of the container, the temperature was increased to 55° C., the contents of the container were constantly stirred. Then the temperature was increased to 80° C. and the contents of the container were constantly stirred for approximately 12 hours. Water (1 milliliter) was added to the contents of the container and the contents of the container were constantly stirred for approximately 2 more hours while be maintained at 80° C. Then the contents of the container were cooled to 65° C. and hydrogen peroxide (1 milliliter) was added to the contents of the container. The contents of the container were constantly stirred and cooled to approximately 20° C. in about 30 minutes to provide Example 1. The contents of the container were then optionally diluted with water (290 milliliters), sodium hydroxide (1 mol/L) was utilized to provide a pH of approximately 7. The solids content of Example 1 was approximately 30 weight percent. The titration analysis of Example 1 indicated a molar ratio of the phosphate surfactant represented by Formula I to the phosphate surfactant represented by Formula II of approximately 82:18.

Example 2, a phosphate surfactant composition, was formed as Example 1 with the change that TERGITOL™ 15-S-7 was utilized rather than TERGITOL™ 15-S-5.

Comparative Example A was RHODAFAC® RS-610.

Properties of Example 1, Example 2, and Comparative Example A are reported in Table 1.

Solid content was determined by weight loss upon drying at 105° C. for two hours.

Appearance was determined by visual inspection.

Surface Tension and Critical Micelle Concentration (CMC) were determined as follows: surface tension was measured on KRUSS Force Tensiometer K100C. Aqueous solution of a surfactant at 10000 ppm as mother solution and water as blank solution were prepared, respectively. The surfactant mother solution was gradually added into the water at a known amount, and the surface tension at different surfactant concentrations were recorded. Surface tension values were plotted against concentration and CMC was determined from the break point of the plot.

Foam height was determined by Ross-Miles Foam Height test: an aqueous solution of surfactant at 0.2% wt. was prepared; then, measurements were carried out according to GB/T-7462-94.

Wetting time was determined as follows: an aqueous solution of a surfactant at 0.5% wt. was prepared; cotton cloth was cut in round shape at the same size (diameter=35 mm). As per GB/T-11983-2008, wetting time of the cotton cloth in the surfactant aqueous solution was recorded.

$Ca^{2+}$ stability was determined according to GB/T-7381-2010.

Alkaline resistance was determined according to GB/T-5556-2003.

TABLE 1

|  | Example 1 | Example 2 | Comparative Example A |
|---|---|---|---|
| Solid content (wt. %) | 32.1 | 28.0 | 25.2 |
| Appearance (20° C.) | Clear, colorless | Clear, colorless | Clear, colorless |
| Surface Tension at CMC (mN/m, 20° C.) | 31.0 | 35.8 | 31.3 |
| CMC (PPm) | 173 | 210 | 250 |
| Foam Height (mm, Ross Miles, 0/5 min at 0.2% wt.) | 130/105 | 135/115 | 145/143 |
| Wetting time (s, 0.5% wt.) | 12.9 | 203.0 | 46.0 |
| $Ca^{2+}$ stability (%, $CaCl_2$, 1% wt. solution) | <0.2% wt. | <0.5% wt. | approximately 0.2% wt. |
| Alkaline resistance (%, NaOH, 1% wt. solution) | 22.4% wt. | 21.4% wt. | 15.3% wt. |

The data of Table 1 illustrates that each of Example 1 and Example 2 have an improved, i.e. reduced, critical micelle concentration, as compared to Comparative Example A.

Further, the data of Table 1 illustrates that each of Example 1 and Example 2 have improved, i.e. reduced, foam height as compared to Comparative Example A.

Example 3, an emulsion, was formed as follows.

Example 1 (3.2 grams [with regards to the solid content of Example 1]), styrene (207.0 grams), 2-ethylhexyl acrylate (170.2 grams), methyl methacrylate (69.0 grams), methacrylic acid (13.8 grams), ammonium bicarbonate (1.38 grams), and water (300 grams) were added to a container and stirred for approximately 30 minutes at a temperature of approximately 20° C. to form a pre-emulsion mixture.

Example 1 (2.3 grams [with regards to the solid content Example 1]) and water (300 grams) were added to a 2-liter jacketed reactor with mechanical stirring and the reactor contents were heated to approximately 87° C. Then, while the temperature was maintained, the pre-emulsion mixture (2 weight percent based upon the reactor contents) and an aqueous solution of ammonium persulfate (1.2 grams ammonium persulfate in 20 grams of water) were added to the reactor contents; the reactor conditions were maintained for approximately 10 minutes for a seed polymerization. Then, over 3 hours, the remaining pre-emulsion mixture and an aqueous solution of ammonium persulfate (1.8 grams ammonium persulfate in 36.8 grams of water) were dropwise added to the reactor contents; one hour following this addition the reactor conditions were maintained at approximately 87° C. to provide reaction time for the emulsion polymerization. Then, the reactor contents were cooled to approximately 45° C. and ammonia water was added to adjust the pH to approximately 7 to 8; thereafter the emulsion was filtered through a 100-mesh cloth filter to provide Example 3.

Example 4, an emulsion, was formed as Example 3 with the change that Example 2 was utilized rather than Example 1.

Comparative Example B, an emulsion, was formed as Example 3 with the change that Comparative Example A was utilized rather than Example 1.

Properties of Example 3, Example 4, and Comparative Example B are reported in Table 2.

Solid content was determined by weight loss upon drying at 105° C. for two hours.

Measurement of polymerization residue was performed as follows: the emulsion was filtered with a filter cloth of 100 mesh. Aggregates collected in the cloth filter were washed by tap water, dried at ambient temperature, and weighed. A percentage by weight of the dried aggregates to the total weight of the emulsion was used as an indication of the polymerization stability. The lower the percentage of the aggregates, the better the polymerization stability was.

Average particle size and its peak width was determined by Zeta Potential Particle Analyzer (Malvern Nano ZS).

$Ca^{2+}$ stability was determined according to GB/T-20623-2006.

TABLE 2

|  | Example 3 (emulsion) | Example 4 (emulsion) | Comparative Example B (emulsion) |
|---|---|---|---|
| Solid content (wt. %) | 46.0 | 45.7 | 45.4 |
| Polymerization residue (g/kg of emulsion) | 0.58 | 0.13 | 0.09 |
| Average particle size (nm) | 87.6 | 90.1 | 92.5 |
| Peak width (nm) | 26.7 | 23.6 | 24.4 |
| $Ca^{2+}$ stability (%, $CaCl_2$, 10% wt. solution) | <0.2% wt. | <0.5% wt. | approximately 0.2% wt. |

Example 5, a coating, was formed as follows.

Deionized water (42 grams), OROTAN™ 681 (7.8 grams, dispersant, obtained from The Dow Chemical Company), Surfynol TG (2 grams, wetting agent, obtained from Air Products), ammonia water (2 grams, 28 weight percent ammonia solution), and Tego Airex 902W (0.46 grams, defoamer, obtained from Evonik) were added to a first container and stirred with a dispersion plate at approximately 400 rpm for 5 minutes; then Ti-Pure R-706 (209 grams, colorant, titanium dioxide) was added to the contents of the first container and the contents were stirred at approximately 2000 rpm for 25 minutes. Then, more deionized water (42 grams) was added to the contents of the first container and the contents were stirred at approximately 400 rpm for 5 minutes.

Example 3 (536.6 grams) was added to a second container and stirred at approximately 400 rpm; deionized water (50 grams) and ammonia water (4 grams, 28 weight percent ammonia solution), were added to the contents of the second container and the contents were stirred at approximately 400 rpm for 5 minutes.

The contents of the first container were added to the second container and were stirred at approximately 400 rpm for 5 minutes. Sodium nitrite solution (8.97 grams, corrosion inhibitor, 15% weight percent sodium nitrite in water), ACRYSOL™ RM-8W (2.1 grams, thickener, obtained from The Dow Chemical Company), UCAR™ Filmer IBT (45.5 grams, coalescent, obtained from The Dow Chemical Company, equivalent to TEXANOL® Ester Alcohol) and deionized water (46 grams) were added to the second container and stirred at approximately 400 rpm for 10 minutes to provide Example 5.

Example 6, a coating, was formed as Example 5 with the change that the Example 4 emulsion was utilized rather than the Example 3 emulsion.

Comparative Example C, a coating, was formed as Example 5 with the change that the Comparative Example B emulsion was utilized rather than the Example 3 emulsion.

Salt spray resistances for Example 5, Example 6, and Comparative Example C were determined according to ASTM B117 utilizing respective 200 μm coatings on metal plates. Resultant salt spray resistance images are shown in FIG. 1. Image 102 shows the Example 5 coating after 24 hours, image 104 shows the Example 6 coating after 24 hours, image 106 shows the Comparative Example C coating after 24 hours, image 108 shows the Example 5 coating after 72 hours, image 110 shows the Example 6 coating after 72 hours, and image 112 shows the Comparative Example C coating after 72 hours. As shown in FIG. 1, each of Example 5 and Example 6 have improved, i.e. reduced, corrosion as compared to Comparative Example C after both 24 hours and 72 hours.

20°, 60°, and 850 gloss for Example 5, Example 6, and Comparative Example C were determined by Portable Glossmeter (micro-TRI-Gloss from BYK); results are reported in Table 3. For gloss, differing values of 1.0 or less are considered to be comparable and differing values greater than 1.0 are considered to be improved, with larger values indicating more desirable gloss.

TABLE 3

|  | Example 5 (coating) | Example 6 (coating) | Comparative Example C (coating) |
| --- | --- | --- | --- |
| Gloss 20° | 23.6 | 22.4 | 9.8 |
| Gloss 60° | 70.1 | 98.1 | 55.2 |
| Gloss 85° | 93.4 | 92.2 | 88.6 |

The data in Table 3 shows that each Example 5 and Example 6 have improved, i.e. increased, gloss as compared to Comparative Example C for each of 20°, 60°, and 85°.

Example 7, an emulsion, was formed as follows.

Example 1 (2.7 grams [with regards to the solid content of Example 1]), styrene (238.0 grams), butyl acrylate (211.0 grams), acrylamide (8.0 grams), acrylic acid (9.5), sodium bicarbonate (0.9 grams) and water (101.0 grams) were added to a container and stirred for approximately 30 minutes at a temperature of approximately 20° C. to form a pre-emulsion mixture.

Example 1 (1.2 grams [with regards to the solid content of Example 1]) and water (283 grams) were added to a 2-liter jacketed reactor with mechanical stirring and the reactor contents were heated to approximately 86° C. Then, while the temperature was maintained, an aqueous solution of ammonium persulfate (1.2 grams ammonium persulfate in 8.0 grams water) was added to the reactor contents and thereafter the pre-emulsion mixture and an aqueous solution of ammonium persulfate (1.8 grams ammonium persulfate in 88.0 grams water) were dropwise added to the reactor contents over three hours; one hour following this addition the reactor conditions were maintained at approximately 86° C. to provide reaction time for the emulsion polymerization; then the reactor contents were cooled to approximately 65° C. and an aqueous solution of sodium formaldehyde sulfoxylate (0.32 grams in 12.0 grams of water) and an aqueous solution of t-butyl hydroperoxide (0.45 grams in 8.0 grams of water) were sequentially added to the reactor contents to provide the emulsion. The reactor contents were kept at 65° C. for 30 minutes, then, were cooled to approximately 45° C. and ammonia water was added to adjust the pH to approximately 7 to 8; thereafter the emulsion was filtered through a 100-mesh cloth filter to provide the Example 7 emulsion.

Example 8, an emulsion, was formed as Example 7 with the change that Example 2 was utilized rather than Example 1.

Comparative Example D, an emulsion, was formed as Example 7 with the change that Comparative Example A was utilized rather than Example 1.

Properties of Example 7, Example 8, and Comparative Example D are reported in Table 4. Properties were determined as previously discussed.

TABLE 4

|  | Example 7 (emulsion) | Example 8 (emulsion) | Comparative Example D (emulsion) |
| --- | --- | --- | --- |
| Solid content (wt. %) | 45.6 | 46.1 | 46.1 |
| Polymerization residue (g/kg of emlusion) | 0.25 | 0.04 | 0.24 |
| Average particle size (nm) | 117.7 | 128.9 | 117.5 |
| Peak width (nm) | 26.6 | 27.6 | 28.0 |
| $Ca^{2+}$ stability (%, $CaCl_2$, 10% wt. solution) | 1.6% wt. | 2.2% wt. | 2.4% wt. |

Example 9, a coating, was formed as follows.

Deionized water (260 grams), CELLOSIZE™ QP-30000H (2 grams, thickener, obtained from The Dow Chemical Company), AMP-95 (2 grams, pH adjuster/dispersant/wetting agent, obtained from Golden Gate Capital) were added to a container while being stirred with a dispersion plate at approximately 450 rpm. OROTAN™ 1288 (4.5 grams, dispersant, obtained from The Dow Chemical Company), ECOSURF™ BD-109 (1 gram, wetting agent, obtained from The Dow Chemical Company), FOAMMASTER® NXZ (1 gram, defoamer, obtained from BASF), were respectively added to the container with stirring at approximately 450 rpm; after the additions the contents of the container were stirred for 10 minutes. Then Ti-Pure R-706 (40 grams, colorant, titanium dioxide), calcined kaolin (125 grams, filler), talcum powder (100 grams, 100 mesh, filler), and calcium carbonate (225 grams, filler) were added to the container with stirring increased to approximately 1800 rpm and maintained for 30 minutes. A third of the contents of the container was utilized for Example 9, a third of the contents of the container was utilized for Example 10, and a third of the contents of the container was utilized for Comparative Example E.

Example 7 (95 grams), FOAMMASTER® NXZ (1 gram), UCAR™ Filmer IBT (9 grams, coalescent, obtained from The Dow Chemical Company, equivalent to TEXANOL® Ester Alcohol), ACRYSOL™ TT-935 (7 grams, thickener, obtained from The Dow Chemical Company), ROMICA™ CF-1100 (2 grams, biocide, obtained from The Dow Chemical Company), BIOBAN™ BPK 114 (1 gram, preservative, obtained from The Dow Chemical Company), and deionized water (113 grams) were added to the container and were stirred at approximately 1800 rpm for 10 minutes to provide Example 9.

Example 10, a coating, was formed as Example 9 with the change that the Example 8 emulsion was utilized rather than the Example 7 emulsion.

Comparative Example E, a coating, was formed as Example 9 with the change that the Comparative Example D emulsion was utilized rather than the Example 8 emulsion.

Color developments for Example 9, Example 10, and Comparative Example E were determined by rub out testing as follows. Red pigment, blue pigment, and black pigment was respectively combined with each of Examples 9-10 and Comparative Example E at a weight ratio of 1:50 (pigment: coating). After stirring, the pigmented coatings were applied (150 μm layers) to a white plate. Immediately thereafter, the coatings were wiped by finger in a gentle, uniform circular fashion (60 circular wipes to form circles having diameters of approximately 3.5 centimeter), while leaving a portion of the pigmented coating untouched. After circle formation, the coatings were maintained at approximately 20° C. for 24 hours. Color development was measured by a Sheen Instruments colorimeter. For the color developments, ΔE indicates color differences between the wiped, circular portions of the coatings and the untouched portions of the coatings, where a larger ΔE indicates a greater color difference between the areas. The results are reported in Table 5.

TABLE 5

|  | Example 9 (coating) | Example 10 (coating) | Comparative Example E (coating) |
|---|---|---|---|
| ΔE (red pigment) | 0.39 | 0.69 | 0.72 |
| ΔE (blue pigment) | 0.93 | 0.53 | 0.84 |
| ΔE (black pigment) | 0.32 | 0.03 | 0.22 |
| ΔE (total) | 1.64 | 1.25 | 1.78 |

The data in Table 5 shows that each Example 9 and Example 10 have improved color development, i.e. lower ΔE total, as compared to Comparative Example E.

200, 600, and 85' gloss for Example 9, Example 10, and Comparative Example E were determined by Portable Glossmeter (micro-TRI-Gloss from BYK); results are reported in Table 6. For gloss, differing values of 1.0 or less are considered to be comparable and differing values greater than 1.0 are considered to be improved, with larger values indicating more desirable gloss.

TABLE 6

|  | Example 9 (coating) | Example 10 (coating) | Comparative Example E (coating) |
|---|---|---|---|
| Gloss 20° | 1.4 | 1.4 | 1.4 |
| Gloss 60° | 3.5 | 3.2 | 3.2 |
| Gloss 85° | 15.6 | 14.6 | 15.5 |

The data in Table 56 shows that each Example 9 and Example 10 have comparable gloss as compared to Comparative Example E for each of 20°, 60°, and 85°.

What is claimed:

1. A phosphate surfactant composition comprising:
a phosphate surfactant represented by Formula I:

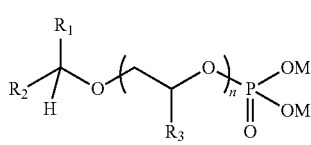

Formula I wherein $R_1$ and $R_2$ are each independently hydrogen or a linear or branched alkyl group having from 1 to 18 carbon atoms, such that a combination of $R_1$ and $R_2$ includes from 8 to 18 carbon atoms; $R_3$ is hydrogen or an alkyl radical containing from 1 to 6 carbon atoms; n is an integer from 1 to 50; and each M is independently hydrogen, an alkali metal atom, an alkaline earth metal atom, an ammonium group, or a substituted ammonium group;

a phosphate surfactant represented by Formula II:

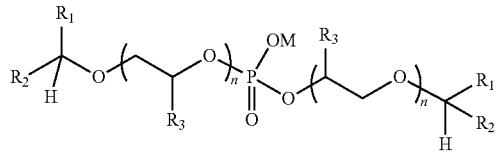

Formula II wherein each $R_1$ and $R_2$ is independently hydrogen or a linear or branched alkyl group having from 1 to 18 carbon atoms, such that combinations of $R_1$ and $R_2$ bonded to a same carbon atom include from 8 to 18 carbon atoms; each $R_3$ is independently hydrogen or an alkyl radical containing from 1 to 6 carbon atoms; n is an integer from 1 to 50; and M is hydrogen, an alkali metal atom, an alkaline earth metal atom, an ammonium group, or a substituted ammonium group; and a secondary alcohol alkoxylate represented by Formula III:

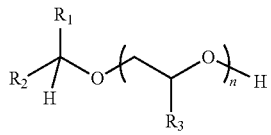

Formula III wherein $R_1$ and $R_2$ are each independently hydrogen or a linear or branched alkyl group having from 1 to 18 carbon atoms, such that a combination of $R_1$ and $R_2$ includes from 8 to 18 carbon atoms; $R_3$ is hydrogen or an alkyl radical containing from 1 to 6 carbon atoms; and n is an integer from 1 to 50;

wherein the phosphate surfactant represented by Formula I is from 20 to 99.9 weight percent, the phosphate surfactant represented by Formula II is from 0.1 to 80 weight percent, and the secondary alcohol alkoxylate represented by Formula III is from 0.01 to 10 weight percent of the phosphate surfactant composition based upon a total weight of the phosphate surfactant composition.

2. An emulsion formed from the phosphate surfactant composition of claim 1.

3. The emulsion of claim 2 wherein the emulsion has a solids content from 25 weight percent to 65 weight percent based upon a total weight of the emulsion.

4. A coating formed from the emulsion of claim 3.

* * * * *